United States Patent [19]
Keeling et al.

[11] Patent Number: 6,143,963
[45] Date of Patent: Nov. 7, 2000

[54] WAXY WHEAT STARCH TYPE HAVING WAXY PROTEINS IN GRANULE

[75] Inventors: Peter L. Keeling; Francie G. Dunlap; Ming Chang, all of Ames, Iowa

[73] Assignee: ExSeed Genetics, L.L.C., Owensboro, Ky.

[21] Appl. No.: 08/944,950

[22] Filed: Oct. 6, 1997

Related U.S. Application Data

[60] Provisional application No. 60/028,264, Oct. 8, 1996.

[51] Int. Cl.$^7$ ............................... A01H 5/00; A01H 5/10; A01H 1/06; A01H 1/04
[52] U.S. Cl. ........................ 800/320.3; 800/320; 800/298; 800/260; 800/263; 800/276
[58] Field of Search ...................................... 800/260, 276, 800/298, 320, 320.3, 263, 278, 284; 47/581, DIG. 1, DIG. 8

[56] References Cited

U.S. PATENT DOCUMENTS 5,502,270  3/1996  Pearlstein et al. ...................... 800/200

FOREIGN PATENT DOCUMENTS

10099/97  10/1997  Australia ......................... A21D 2/36

OTHER PUBLICATIONS

Nakamura et al. Production of waxy (amylose free) wheats. Molecular and General Genetics. vol. 248, pp. 253–259, 1995.

Oda et al. A bread wheat mutant with low amylose content induced by ethyl methylsulfonate. Japanese Journal of Breeding. vol. 42, pp. 151–154, 1992.

Vrinten et al. Molecular characterization of waxy mutations in wheat. Molecular and General Genetics. vol. 261, pp. 463–471, 1999.

Zhao et al. An improved 1–D SDS–Page method for the identification of three bread wheat 'waxy' proteins. Journal of Cereal Science. vol. 23, pp. 191–193, 1996.

Hoshino et al. Breeding Science, vol. 46, pp. 185–188, 1996.
Yasui et al. Breeding Science, vol. 47, pp. 161–163, 1997.
Ainsworth et al., "Expression, organisation and structure of the genes encoding the waxy protein (granule–bound starch synthase) in wheat" Plant Molecular Biology, 1993, vol. 22, pp. 67–82.

Okagaki et al., "A Deletion Common to Two Independently Derived waxy Mutations of Maize" Genetics, Jun. 1991, vol. 128, pp. 425–431.

Nakamura et al., "Production of waxy (amylose free) wheats" Molecular and General Genetics, 1995, vol. 248, pp. 253–259.

Visser et al., "Reviews: Towards Modifying Plants for Altered Starch Content and Composition" Trends in Biotechnology, 1993, vol. 11, pp. 63 and 66–68.

Yamamori et al., "Production of a Waxy Wheat By Genetically Eliminating Wax Proteins" Gamma Field Symposia No. 33 (reprinted), 1994 Institute of Radiation Breeding, NIAR, MAFF, Japan.

Yong–Cheng Shi et al., "The Structure of four waxy starches related to gelatinization and retrogradation" Carbohydrate Research, 227 (1992) pp. 131–145.

Hayakawa et al., "Quality Characteristics of Waxy Hexaploid Wheat (*Triticum aestivum* L.): Properties of Starch Gelatinization and Retrogradation" Cereal Chemistry 1997 74(5):576–580.

Kiribuchi–Otobe et al., "Production of Hexaploid Wheats with Waxy Endosperm Character" Cereal Chemistry 74(1):72–74, 1997.

Biliaderis, "Physical Characteristics, Enzymatic Digestibility, and Structure of Chemically Modified Smooth Pea and Waxy Maize Starches" J. Agric. Food Chem. 1982, 30, 925–930.

Crookston, "The story of waxy corn" Crops and Soils Magazine/Aug.–Sep. 1979, pp. 11–13.

Zhao et al., "An Improved 1–D SDS–Page Method for the Identification of Three Bread Wheat Waxy Proteins" Journal of Cereal Science 23 (1996) 191–193.

Abstract of JP 6125669 "Identification of Wx gene—by sepg. Wx proteins using iso–electric electrophoresis" 1992.

*Primary Examiner*—Gary Benzion
*Assistant Examiner*—Melissa L. Kimball
*Attorney, Agent, or Firm*—Nixon & Vanderhye PC

[57] ABSTRACT

Broadly, the present invention relates to mutating starch genes in polyploid cereal grains. Specifically, this invention concerns mutant wheat plants, mutant wheat grain and the starch therefrom.

12 Claims, No Drawings

WAXY WHEAT STARCH TYPE HAVING WAXY PROTEINS IN GRANULE

This application claims the benefit under Title 35 U.S. States Code section 119(e) of U.S. provisional application 60/028,264 filed on Oct. 08, 1996.

FIELD OF THE INVENTION

Broadly, the present invention relates to mutating starch genes in polyploid cereal grains. Specifically, this invention concerns mutant wheat plants, mutant wheat grain and the starch therefrom.

BACKGROUND

Cereal grains, such as rice, wheat, corn and barley help to feed the world's population. A large percentage of the world population's staples are formed of these grains. These grains are processed to make breads, cereals, pasta, flour, etc. Processed grains have different qualities which lead to different product uses. Wheat grains are processed into wheat flour, which is a storehouse of nutrients. The starch, protein, lipids, enzymes, and nutrients affect, in differing degrees, the flour product. Starch in the flour product affects its characteristics to a large degree. The digestibility, processing temperatures, cooking qualities of flour are all impacted by the type of starch used.

Starch is formed of two components amylose and amylopectin. At least one of these components is altered in a number of diploid cereal grains which have starch mutations. One starch mutation is referred to as the waxy mutation. Cereal grains having the waxy mutation form low amylose starch. Naturally occurring waxy mutants are well known in rice and maize, both diploid species. However, naturally occurring starch mutants are not known in polyploid species. To alter the starch in a polyploid species requires several independent mutations. Wheat seldom has naturally occurring mutants because both soft and hard wheats are hexaploid, although durum wheats are tetraploid. No one has discovered a naturally occurring waxy wheat.

Wheat (*Triticum aestivum* L.) has three chromosome sets derived from three different species. Each chromosome set has a genome letter, A, B or D. A wheat waxy mutant would have homozygous waxy alleles in each of the A, B & D chromosomes. Mutations in wheat have been identified by protein characterization in the individual A, B & D genomes. Until 1992 these protein characterizations detected only a single waxy protein band. The test was not able to distinguish a protein band for each of the three genomes. If one of the three genomes was not producing a protein this test could not detect it. A modified detection system using SDS-PAGE with low BIS acrylamide concentration and a two-dimensional gel electrophoresis (2-D PAGE) showed two of the expected three protein bands. The third band was detected by using isoelectric focusing (IEF) for the first dimension and the modified SDS-PAGE for the second. The modified detection system detected three protein bands. Each protein band corresponds to one of the A, B and D sets of chromosomes. By detecting the individual proteins wheat lines could be screened for null waxy alleles. A null allele does not produce a certain protein at that allele on a certain chromosome. A null mutant does not produce a certain protein at any of the chromosomes. This is in contrast to a non-null mutant which does produce the protein, but in an inactive state.

Once a test showing the three bands was identified a number of researchers began to screen waxy wheat for null alleles. Single null alleles were located when individual starch proteins were missing from wheat starch. Single null waxy wheat alleles were identified in only about 10% of the US winter wheat germplasm. The remaining wheat were wildtype having three functional wx loci. R. A. Graybosch reported on a few single null waxy alleles in both the A and B genomes. Only two single nulls are known to exist in the D genome. One single null D genome waxy allele has been reported in Japan and one has been reported in Canada.

Recently, researchers discovered four separate double null waxy alleles in wheat. Each of these double null waxy alleles (partial mutants) were null for waxy alleles of the A and B genome. The Japanese reported the Kanto lines 79, 107, Saikai 173 and R. A. Graybosch reported Ike. Ike is a public line, developed by the Kansas University breeding program. These double null waxy partial mutants are the only ones known to exist. However, with the modified screening procedure researchers can expect the discovery of additional single and double null alleles. Like single waxy nulls, these newly discovered double null waxy partial mutants, still produce a waxy protein in the D allele and thus still have significant amylose content. However, the double null waxy partial mutants amylose content is recognizably less then single waxy nulls.

Even after the discovery of the double nulls there still was needed a waxy wheat mutant plant that had a waxy mutation in all three genomes. In 1994, a waxy wheat plant free of waxy protein was produced. The Bai Huo Chinese cultivar lacking a waxy protein was crossed on to Kanto 107 and Saikia 173. Out of 720 F2 seeds 14 were free of Wx proteins.

Conventional crossing of a partial null mutant with a single null allele did produce a waxy wheat. It also produced an entirely new combination of genes within the chromosomes of the resultant waxy wheat. To generate useful lines from the resultant waxy wheat plant breeding was used. The waxy wheat was selfed and the progeny were selected for agronomics traits and the waxy trait throughout breeding generations. Although conventionally bred plants having the waxy mutation are easily identified by the iodine test; agronomic traits are much more difficult to identify. Agronomic traits are often multigenetic and in wheat these are further complicated by three separate sets of chromosomes. Reconstruction of the three chromosomes with conventional breeding, or even with dihaploidy takes time and a number of crosses. Even after a number of crosses, the waxy wheat is not essentially identical to one parent, it is only similar to the parent.

A plant which is essentially identical to the parent plant is an isogenic line. An isogenic line is characterized by essentially identical genes. Forming a waxy wheat that is isogenic to its parent avoids conventional breeding problems. There is a need for a method of forming a waxy wheat that does not produce an entirely new combination of genes within the chromosomes of the waxy wheat. There is a need for an efficient method for forming full mutants from double chromosome mutants or double chromosome mutants, from single chromosome mutants in polyploid cereals. In other words, there is a need for a method to form isogenic polyploid lines which contain mutations.

Additional needs develop, once an isogenic starch mutation is in commerce. Breeders will breed with this isogenic germplasm to place the starch mutation into other germplasm. To maintain germplasm security, there is a need for a method of identifying the mutation. If the mutation is identified then misuse of germplasms can be identified.

SUMMARY OF THE INVENTION

An object of the present invention is a method of forming polyploid isogenic seeds and plants which differs from the parent by being a starch mutant.

Still another object of the present invention is an isogenic wheat seed and plant that produces waxy starch.

A further object of the present invention is a method of identifying isogenic lines by fingerprinting the modified starch the lines produce.

Yet a further object of the present invention is waxy wheat starch which contains an inactive protein in at least one of the waxy loci.

In addition, another object of the present invention is the method of mutating polyploid cereals to form a modified starch.

The present invention broadly encompasses a method of making a full mutant allele polyploidy cereal seed. This method includes the following steps. Treating a double mutant allele in a polyploid plant material with a mutagen. This forms treated plant material. The treated plant material is then screened to identify full mutant allele plant material. The full mutant allele plant material are selected. The present method can also include the additional steps of selecting polyploid plant material having a single mutant allele and treating this plant material with a mutagen then screening the plant material to identify plant material that contain a double mutant allele. This plant material is then used in the earlier method to form the full mutant allele. A number of mutagens can be employed but the EMS mutagen is preferred as it makes point mutations. The method can be performed on plant material such as wheat seeds. In this method the double mutant allele can be a double null allele or the double null allele can be a double null waxy allele. The screening can include a test for opaqueness. The step for screening can also include testing starch with iodine. The full mutant allele seeds stain red when tested with iodine.

The present invention also encompasses a product. A polyploidy plant material having either no proteins or inactive protein produced in one allele in all sets of chromosomes and at least one of the alleles containing a point mutation due to application of mutagens. This plant material can also include at least one allele in one set of chromosomes producing an inactive protein due to said point mutation.

The polyploid plant material in accordance to the present invention includes isogenic polyploid plant material that contains at least one mutagen induced point mutation in a specific allele in at least one set of chromosomes and at least one naturally occurring mutation in the same specific allele in a different set of chromosomes. In addition the present invention includes the starch produced there from. The progeny of this plant material is within the scope of the present invention.

More specifically, the present invention encompasses double null mutant alleles in polyploidy plant material that is formed into full mutant alleles by mutagens. The present invention particularly includes a waxy 60 mutant plant material and the starch therefrom. This waxy 60 mutant can be formed from a number of waxy partial mutants. Specifically it can be formed from IKE. The present invention includes isogenic lines to a wheat parent line that contains a full mutant waxy allele. Particularly, the present invention encompasses isogenic lines to IKE, Kanto lines 79, 107, Saikai 173 and Bia Huo that contain a full mutant waxy allele and the waxy starch therefrom. The present invention also includes a isogenic wheat plant with a full mutant starch allele and at least one fingerprint protein.

The present invention also includes a method of identifying ancestry of polyploid material by isolation of the fingerprint proteins of the starch. Additionally, the present invention includes the method of identifying the fingerprint protein in the starch of waxy wheat.

DESCRIPTION OF THE INVENTION

Definitions

Single null *allele—no protein produced in one allele in one set of chromosomes.

Double null *allele—no protein produced in one allele in two sets of chromosomes.

Full null *allele—no protein produced in one allele in all sets of chromosomes.

Single inactive *allele—an inactive protein produced in one allele in one set of chromosomes.

Double inactive *allele—an inactive protein produced in one allele in two sets of chromosomes.

Full inactive *allele—an inactive protein produced in one allele in all sets of chromosomes.

Single mutant *allele—no protein produced in one allele in one sets of chromosomes or an inactive protein produced in one allele in one set of chromosomes.

Double mutant *allele—no protein produced in one allele in two sets of chromosomes or an inactive protein produced in one allele in two sets of chromosomes.

Full mutant *allele—no protein produced in one allele in all sets of chromosomes or an inactive protein produced in one allele in all sets of chromosomes.

Waxy partial mutant—having no waxy proteins or inactive waxy proteins produced in one allele in two sets of chromosomes.

Waxy 60 mutant—having either no waxy proteins or inactive waxy protein produced in one allele in all sets of chromosomes but at least one allele in one set of chromosome producing an inactive waxy protein.

New full mutant—having either no proteins or inactive protein produced in one allele in all sets of chromosomes but at least one allele in one set of chromosome producing an inactive protein.

*Identifying terms may be added such as starch, waxy, ae, dull, sugary2 ,etc.

Broadly, the present invention produces mutated starch plants by mutagenesis, in polyploid cereal grains. Such new starch mutant plants are produced more efficiently than starch mutant plants produced by conventional breeding or even biotechnology-aided breeding. The mutant plants of the present invention alter the starch. One type of altered starch is waxy starch. This invention particularly includes the production of waxy polyploid plants. More specifically this invention includes waxy wheat plants. More specifically waxy 60 mutant polyploidy grain.

The waxy wheat plant invention is formed from a double null waxy allele wheat mutated with ethyl methane sulfonate (EMS). The resultant waxy 60 mutant wheat plant produces waxy starch containing a 60 kDa bound starch synthase protein (it is not null for all 3 waxy alleles). This inactive 60 kDa bound starch synthase protein identifies the present invention. The present invention can be distinguished by the presence in starch extracts of this inactive 60 kDa bound starch synthase protein from existing waxy wheat. Like all waxy wheat starch, the wheat starch of the present invention stains red with iodine. This red stain identifies the starch as waxy starch. Unlike all presently existing waxy wheat starch, the present invention has a 60 KDa waxy protein band that appears when the starch proteins are extracted and separated by SDS-gel electrophoresis. This fingerprint protein of the present invention is also identifiable by use of antibodies specific to the waxy protein.

In rare instances, the EMS mutation may stop the 60 KDa protein from forming in the starch. This rare plant would be a triple null in the waxy allele without a fingerprint. A triple null waxy plant and a plant with a double null with an inactive 60 KDa protein in the waxy allele produce the same waxy starch with the exception of the presence of the 60 KDa protein in the starch of the later. Although in this rare instance the waxy starch would appear the same as the prior art starch the plants would still be very different. Isogenic plants are plants that have essentially identical genes. Plants of the present invention are isogenic and plants formed by breeding and haploidy are a mixture of genes from two sources. The term plant includes all plant parts including cells, leaves, roots, meristems, stems, flowers, seeds, and pollen.

The isogenic line of the present invention once produced can be bred through traditional breeding methods or marker breeding methods to move the starch mutant alleles into different wheat germplasm, or to move different alleles into the starch mutant wheat. The waxy trait is retained in the breeding process if the iodine stains red.

The present invention is a repeatable method of mutating polyploid plants to form isogenic plants with starch mutations. A polyploidy plant having at least one starch mutation in one set of chromosomes is selected. This plant is mutated by EMS. This method of mutagenesis forms an isogenic plant with a point mutation. The resultant plants are screened for the desired point mutation that give the desired starch. If the waxy mutation is the desired mutation then the screening is for opaqueness of the seed. Further screening of these seeds can be achieved by staining the starch in the seed with iodine. Seeds with starch that stains red are waxy.

Generally then the method of the present invention is selecting a polyploid plant with an existing starch mutation in at least one set of chromosomes, mutating the selected plant and screening for the mutation in the other set of chromosomes. Each step of the method can vary slightly. For example the selection can be done by a protein isolation test such as the modified SDS-PAGE, or by a phenotype test. Once selected, the germplasm may have to be increased to have sufficient plant material for the mutation step.

The mutation step can be done by a number of mutagenesis methods. These methods mutate plant material with a suitable mutagens. These mutagens can be used on the pollen, the fruit, the anthers, the seeds and the ovum of different plants. The most preferred method is treatment of seed or pollen with the mutagens. The mutagens can be, chemical or physical. Chemical agents include but are not limited to ethyl methane sulfonate, diazo reagents, N-nitroso, N-methyl glycine, psoralens and physically by ultraviolet light, X-rays, gamma ray and any other agents having similar effects may also be used. The more preferred group of mutagens includes the use of sodium azides or nitrosoguanidine, or any alkylating agent like ethyl methane sulfonate (EMS). The most preferred agent being EMS. The EMS method is outlined in the Neuffer paper in the Maize Genetic Newsletter 45 PAGE 146 (1971).

The EMS method generates a point mutation in the nucleotide sequence of the gene. Some of the other methods cause more gene disruption than a point mutation. EMS mutates more specifically and does not change most of the plant's genome. The present invention thus forms lines that are isogenic to the parent line and include the new point mutation. The point mutation is an inheritable genetic change in the DNA of the plant. The genetic change is called an induced mutant allele which means a mutation in the plant genome that was introduced into the plant or an ancestor of the plant by application of a mutagens and not by transformation.

The final step is screening to identify plants grown from the mutated seeds that carry the starch mutation in the additional set of chromosomes. The screening can be based on phenotypic traits, starch components, starch characteristics and the like.

This general method of forming isogenic lines from polyploid cereals was used to form a waxy wheat isogenic to IKE. In this specific use of the method, IKE, a double null waxy allele, ( an A,B double null wheat seed) was selected. Ike seed was planted and the self pollinated seed was harvested. The harvested grain (or seeds) were mutated with EMS. The number of treated seeds was large enough to produce the desired mutation events. The probable number of desired mutation events is a function of genetics and polyploidy. This number can be calculated by one of ordinary skill in the art. When Ike was mutated, the desired event, which is a point mutation in the waxy allele of the D genome occurred, in one out of every 600 plants. These plants carried a single inactive waxy allele and a double null waxy allele. To maximize the waxy 60 mutant plants (having an additional mutation in the waxy allele of the D genome), 15 pounds of Ike seeds were mutated in an EMS solution for 16 hours then rinsed thoroughly. The treated seeds were planted. The wheat seed was grown, fertilized, herbicide-treated, and insecticide treated as was appropriate. The wheat when ready to harvest was hand-harvested. Mechanical harvesting can be used, but may result in less useable seeds. The hulls on the seeds were removed for seed screening. The seeds were screened for the desired starch trait by viewing the seed on a light box and approximately 60 opaque seeds were selected from a small number of seeds. These selected seeds were then stained with iodine. Distant from the embryo, the seeds were cut with a razor. The iodine was applied to the cut portion of the seed. If the stain was red the seed was waxy wheat, if the stain was not red, the seed was discarded. The selected waxy 60 mutant IKE seeds were planted to increase seed.

Experiment One

Mutating IKE

Fifteen pounds of Ike wheat seeds were soaked in 77 grams of liquid EMS in 15.4 liters of water. First 9 liters of water had 77 grams of EMS added. The EMS dropped down into the bottom of the container. To mix the EMS uniformly an air hose bubbled air in the solution. Then 6.4 additional liters were added to the solution. The concentration of EMS solution was 77 g/15400 ml=0.5%. Then, the 15 pounds of Ike seed was added to the solution. The amount of EMS per seed was 77,000 mg/24,160=0.32 mg/per seed.

The seeds in the solution were bubbled with air for 20 hours. A sieve was used to take the seeds out of the solution. The seeds were mixed with coarse sand, style #97591, size large, made in China to absorb the surface water and dry the seeds.

The seeds were directly planted in the field within six hours of removal from the water. The germination rate of the treated seed was good. The seed was planted and treated in the manner normal winter wheat with the exception that at maturity the wheat heads were hand harvested. Hand harvesting avoided excess damage to the heads. This experiment can be repeated with any of the double null wheat lines.

This procedure forms isogenic seeds with the added point mutation. The isogenic seeds were then screened for the point mutations giving the waxy mutation.

Experiment Two

Screening for Waxy

After the treatment described in experiment one the harvested wheat were threshed individually. The heads were threshed using a thresher (Almaco, Inc.) which utilized a rasping motion produced by two belts running in the same direction at different speeds. Chaff was blown away and, simultaneously, the seed from each head was stored in a coin envelope.

Seed was analyzed for waxy starch by screening the seed for opaqueness. The opaqueness of the seed was viewed with polarized fluorescent lighting. Using a fluorescent light box and a polarizing sheet, seeds from individual heads were visually screened. Those seeds which were not translucent were identified. These opaque seeds were then separated for further testing.

The opaque seeds were tested using an iodine staining procedure. A section of the endosperm was cut and exposed to a 2 μL drop of potassium iodine solution (2 g $I_2$, 20 g Kl in 1L $H_2O$) for 10 seconds. This portion of the endosperm was observed for color change under a low power microscope. A reddish-brown color indicated an endosperm starch of approximately 100% amylopectin (waxy) while a blue color indicates it is not a waxy. These two screens confirmed the presence of the waxy mutant in seeds of the mutagenized wheat.

The waxy wheat formed by the present invention produced waxy starch. The prior art, conventionally bred by crossing double A, B nulls plants with D null plants forms a waxy wheat. However, there are a number of differences between the present invention and the prior art. One difference is that the present invention rarely forms a null mutation. The mutation of the present invention is non null. The prior art is all null mutations.

The present invention forms isogenic plants and seeds. In other words, the invention is essentially identical to its parent but includes that point mutation. In contrast the prior art does not form an isogenic plant. The prior art plant is similar to both parents.

The present invention forms an inactive protein in the starch. The prior art does not. The present invention's inactive protein is a fingerprint in its starch. In other words the isogenic plant of the present invention can be identified from the prior art by its starch. Identification is useful to protect germplasm. If an isogenic line of the present invention is used in a breeding program to introgress the waxy trait into a new line the fingerprint protein will be present. Thus the source of the waxy mutation can be identified as coming from an isogenic line of the present invention. Misuse of the germplasm can be traced by the fingerprint protein. The fingerprint protein can be used for even more precise identification of the germplasm. The amino acid sequence of the protein has a point mutation relative to wildtype amino acid sequence. Thus if the amino acid sequence in the starch of a suspected plant has the same amino acid as starch from the mutated plant then the plant's parentage is known to come from the present invention.

The fingerprint has two primary uses, one for fingerprint identification of the parentage and two to identify desired starch mutations. If the present invention was the isogenic IKE waxy then the starch will only contain one inactive 60 kDa protein. If it is known that there is only one protein then a standard SDS-PAGE can be used to isolate the protein. A standard SDS-PAGE is outlined below. If there is more than one possible protein then the modified SDS-PAGE and 2D-PAGE that is described in MAKOTO YAMAMORI and TOSHIKI NAKAMURA.(1994) Production of a Waxy Wheat by Genetically Eliminating Wx Proteins. Gamma Field Symposia No. 33 Institute of Radiation Breeding NIAR, MAFF Japan pages 63–74 should be used. (The details of these prior art methods are more thoroughly described in KAGAWA, H., HIRANO, H., and KIKUCHI, F. (1988). Variation of glutelin seed storage protein in rice (oryza sativa L.). Jpn. J. Breed. 38: 327–332.and O'FARRELL, P. H. (1975), High resolution two-dimensional electrophoresis of proteins. J. Biol. Chem. 250: 4007–4021.) If desired starch mutations are identified by a simple visual test then protein isolation is probably not necessary. But a number of starch mutations in polyploid grains are not identified visually. For these starch mutants the protein of the seed can be isolated and identified. A method for isolating protein from the starch granule is given as follows:

Starch-Granule Protein Isolation

Homogenize 12.5 g grain in 25 ml Extraction buffer (50 mM Tris acetate, pH7.5, 1 mM EDTA, 1 mM DTT) for 3×20 seconds in waring blender with 1 min intervals between blending. Keep samples on ice.

Filter through mira cloth and centrifuge at 6,000 rpm for 30 min.

Discard supernatant and scrape-off discolored solids which overlay white starch pellet.

Resuspend pellet in 25 ml buffer and re-centrifuge. Repeat washes twice more.

Resuspend washed pellet in ⁻20° C. acetone, allow pellet to settle at −20° C. Repeat.

Dry starch under stream of air (Store at −20° C.)

Protein Extraction

Mix 50 mg starch with 1 ml 2% SDS in eppendorf.

Vortex, spin at 18,000 rpm, 5 min, 4° C. Pour off supernatant. Repeat twice.

Add 1 ml sample buffer (4 ml distilled water, 1 ml 0.5M Tris-HCL, pH6.8, 0.8 ml glycerol, 1.6 ml 10% SDS, 0.4 ml B-mercaptoethanol, 0.2 ml 0.5% bromphenol blue).

Boil eppendorf for 10 min with hole in lid.

Cool, centrifuge 10,000 rpm for 10 min. Decant supernatant into new eppendorf. Boil for 4 minutes. Cool.

SDS-Page Gels

|  | 10% Resolve | 4% Stack |
| --- | --- | --- |
| Acryl/Bis 40% stock | 2.5 ml | 1.0 ml |
| 1.5M Tris pH 8.8 | 2.5 ml | — |
| 0.5M Trip pH 8.8 | — | 2.5 ml |
| 10% SDS | 100 μl | 100 μl |
| Water | 4.845 ml | 6.34 ml |
| Degas 15 min |  |  |
| 10% Ammonium Persulfate | 50 μl | 50 μl |
| TEMED | 5 μl | 10 μl |

Mini-Protean II Dual Slab Cell 3.5 ml 10% acrylamide Resolve buffer per gel. 4% acrylamide Stack on top. 200V Constant. 10× Running buffer (250 mM Tris, 1.92M glycine,1 % SDS, pH 8.3).

Bound Starch Synthase

1. Extract Preparation a) Tissue concentration 100 mg/2 ml extraction buffer.

b) Polytron at full speed for 20 seconds at 4° C.

c) Centrifuge in a SM24 rotor at 17500 rpm, 20 mins, 4° C.

d) Save extract for soluble enzyme assays and resuspend pellet in 2 ml of extraction buffer and treat as above.

e) Repeat wash two more times and resuspend in a final volume of 1 ml.

2. Assay (200 ul)

| Reagent | Conc. | Amount |
| --- | --- | --- |
| Bicine (pH 8.3) | 100 mM | 20 $\mu$mole |
| EDTA | 4.5 mM | 0.9 $\mu$mole |
| KCL | 25 mM | 5 $\mu$mole |
| Glutathione | 10 mM | 2 $\mu$mole |
| Glycogen | 10 mg/ml | 2 mg |
| ADPG [14C] | 73.5 mM | 1500 nmole |
|  | (444 dpm/nmol) | (88,800 dpm) |

3. Stock Solutions

| A) Buffer | For 50 mls |
| --- | --- |
| 200 mM Bicine (pH 8.3) | 1.632 g |
| 9 mM EDTA.Na$_2$ | 167 mg |
| 50 mM KCL | 186 mg |
| 20 mM GSH | 307 mg* |

B) Glycogen 160 mg/2 ml (prefer rabbit liver vs. oyster)

| C) ADPG [14C] | For lots of 1.25 ml |
| --- | --- |
| 60.0 mM ADPG | 53.5 mg ADPG (check purity and Theo. MW) |
|  | Theo. MW = 684.9, purity = 96% |
|  | +77 $\mu$l/2 $\mu$Ci ADPG [14C] + |
|  | 1.173 ml H$_2$O. Store at −20C |

4. Procedure

A) Add to an eppendorf tube

100 $\mu$l buffer (preincubated at assay temperature)

25 $\mu$l glycogen

50 $\mu$l extract

B) Incubate tubes for 2 minutes at required temperature.

C) Start reaction by adding

25 $\mu$l ADPG[14C].

D) After 20 minutes, stop the reaction by adding

100 $\mu$l .025N NaOH 1.0 ml Methanol

E) Hold on ice for 5 minutes, spin in microfuge 5 minutes at full speed, 4 C aspirate discard supernatant, wash pellet 2 times by dissolving in 300 $\mu$l 0.1 N NaOH, reprecipitate with 1.0 ml Methanol.

F) Dissolve pellet in 1 ml 1.0M HCL and boil for 10 minutes.

G) Cool the solution and add 0.9 ml reaction mixture to vial and add 10 ml of "Ready Safe" cocktail.

5. Calculation 0.9 ml (counted portion)×2(dilution factor)×1000 $\mu$l (total extract vol)×1000 mg 1.0 ml (total vol)×50 $\mu$l (assay extract vol)×50 mg (tissue wt)×20(min)

Other Embodiments

Part Waxy Wheats—Description

Several single-null allele wheats are known and can be found by screening starches for the waxy proteins derived from the A, B or D genomes of hexaploid wheats. Such single-null allele genotypes can be converted to partial waxy-types using mutagenesis using the same methods and techniques outlined herein for the double null allele genotypes. The method of mutating a single null allele to form a double null allele is the same except the screening of the final product is different. This isogenic line with one additional starch mutation can not usually be identified by the modified SDS-PAGE. The new isogenic line with a point mutation would produce starch that has the same protein banding as the starch from the non EMS treated plant. To identify a single null allele with a point mutation in the waxy allele of a different chromosome requires a different test. In the waxy starch mutation the identifying test is in the reduction in the percentage of amylose in the starch of the EMS treated plants having the desired mutation. Of course, once the EMS process is used to form a partial mutant then the partial mutant can be used to form a full waxy mutant. The partial waxy is mutated and screened by the light box and iodine test described above. Accordingly, it can be seen that this repeatable method will produce a wheat variety and low amylose content. Such waxy wheat starches are useful in a variety of food and feed applications. Waxy wheat starch could substitute for waxy maize in a number of food and feed applications, for example in extending shelf-life of a variety of baked products and in gelling pies.

Although the description above contains examples, these should not be construed as limiting the scope of the invention. They provide illustrations of some of the presently preferred embodiments of this invention.

We claim:

1. A full waxy starch mutant allele polyploidy wheat plant, said plant comprising:

a polyploid set of chromosomes, a mutation in the starch waxy allele of each set of said chromosomes, wherein at least one of such mutations produces a non-null waxy protein.

2. A non-null waxy polyploid wheat plant.

3. Progeny of the plant of claim 2 which are non-null waxy polyploid wheat.

4. A waxy wheat starch granule from the plant of claim 2.

5. Progeny of the plant of claim 1 which are non-null waxy.

6. A waxy wheat starch granule from the plant of claim 1.

7. A full non-null waxy polyploid wheat plant which has been produced from a parent plant by mutagenesis with a mutagen to produce said non-null in a waxy gene which encodes a non-null waxy protein.

8. Progeny of the plant of claim 7 with a genotype which is full non-null in the waxy gene.

9. A waxy polyploid wheat seed which is non-null at the waxy allele.

10. Seed of the plant of claim 2 which are non-null waxy polyploid wheat.

11. Seed of the plant of claim 1 which are non-null waxy.

12. Seed of the plant of claim 7 with a genotype which is full non-null in the waxy gene.

* * * * *